(12) United States Patent
Bishop et al.

(10) Patent No.: US 8,529,725 B2
(45) Date of Patent: Sep. 10, 2013

(54) PRINTED ABSORBENT ARTICLE COMPONENTS FOR A UNIFORM APPEARANCE

(75) Inventors: David Fleger Bishop, Appleton, WI (US); Patsy Ann Krautkramer, Omro, WI (US); Julia Hartono, Greenville, WI (US); Katherine Carol Wheeler, Menasha, WI (US); Marcille Faye Ruman, Oshkosh, WI (US); Daniel Robert Schlinz, Greenville, WI (US); Kimberly Marie Downs, Oshkosh, WI (US); Tami Lynn Kurtz, Oshkosh, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 994 days.

(21) Appl. No.: 12/580,882

(22) Filed: Oct. 16, 2009

(65) Prior Publication Data

US 2011/0092943 A1    Apr. 21, 2011

(51) Int. Cl.
*B29C 65/00* (2006.01)
*B32B 37/00* (2006.01)
*B32B 38/14* (2006.01)

(52) U.S. Cl.
USPC .......................................... 156/277; 156/324

(58) Field of Classification Search
USPC .............................. 156/277, 324; 604/385.29
See application file for complete search history.

(56) References Cited

U.S. PATENT DOCUMENTS

| | | |
|---|---|---|
| 4,623,342 A | 11/1986 | Ito et al. |
| 5,458,590 A | 10/1995 | Schleinz et al. |
| 5,503,076 A | 4/1996 | Yeo |
| 5,575,782 A | 11/1996 | Hasse et al. |
| 5,612,118 A | 3/1997 | Schleinz et al. |
| 5,643,243 A | 7/1997 | Klemp |
| 5,681,302 A | 10/1997 | Melbye et al. |
| 5,766,389 A * | 6/1998 | Brandon et al. ................. 156/64 |
| 5,807,368 A | 9/1998 | Helmer |
| 6,352,528 B1 | 3/2002 | Weber et al. |
| 6,537,935 B1 | 3/2003 | Seth et al. |
| 6,569,136 B1 | 5/2003 | Tao et al. |
| 6,596,918 B1 | 7/2003 | Wehrle et al. |
| 6,649,808 B1 | 11/2003 | Tao et al. |

(Continued)

FOREIGN PATENT DOCUMENTS

| | | |
|---|---|---|
| EP | 1 704 842 A1 | 9/2006 |
| EP | 1 964 533 A2 | 9/2008 |
| JP | 2003-070838 A | 3/2003 |
| WO | WO 01/49230 A1 | 7/2001 |

*Primary Examiner* — Sing P Chan
(74) *Attorney, Agent, or Firm* — Randall W. Fieldhack; David J. Arteman; R. Joseph Foster, III

(57) ABSTRACT

A method is presented for manufacturing a disposable absorbent article having multiple components including selecting a first material appropriate for use as an outer cover; producing a chassis including the outer cover, the outer cover including an outer cover central region having an outer cover central region appearance; selecting a second material appropriate for use as an elastic panel, wherein the second material is different from the first material; and producing a first elastic panel having a first elastic panel central region. The method also includes printing the first elastic panel central region with a first elastic panel printed graphic; and attaching the first elastic panel to the chassis, wherein the selecting and printing are performed such that the first elastic panel central region gives the appearance of being substantially similar to the outer cover central region appearance.

14 Claims, 5 Drawing Sheets

(56) References Cited

U.S. PATENT DOCUMENTS

| | | |
|---|---|---|
| 6,652,497 B1 | 11/2003 | Suprise |
| 6,702,795 B2 | 3/2004 | Klemp |
| 6,706,030 B1 | 3/2004 | Okuda et al. |
| 6,719,742 B1 | 4/2004 | McCormack et al. |
| 6,949,689 B2 | 9/2005 | Noda et al. |
| 7,118,558 B2 | 10/2006 | Wu et al. |
| 7,169,137 B2 | 1/2007 | Shimada |
| 7,178,571 B2 | 2/2007 | Vergona |
| 7,311,696 B2 | 12/2007 | Christon et al. |
| 7,378,130 B2 | 5/2008 | Coronado et al. |
| 7,416,777 B2 | 8/2008 | Nair et al. |
| 7,432,413 B2 | 10/2008 | Roe et al. |
| 2002/0002358 A1* | 1/2002 | Durrance et al. ........ 604/385.01 |
| 2003/0088226 A1 | 5/2003 | Takagi et al. |
| 2004/0122398 A1 | 6/2004 | Schnabel et al. |
| 2005/0015066 A1 | 1/2005 | Anderson et al. |
| 2005/0154365 A1 | 7/2005 | Zander et al. |
| 2006/0003657 A1 | 1/2006 | Larson et al. |
| 2006/0021536 A1 | 2/2006 | Song et al. |
| 2006/0025736 A1 | 2/2006 | Berg et al. |
| 2006/0161130 A1 | 7/2006 | Zacharias et al. |
| 2007/0049889 A1 | 3/2007 | Larson et al. |
| 2007/0142800 A1 | 6/2007 | Liu |
| 2008/0000003 A1 | 1/2008 | Melander |
| 2008/0058748 A1 | 3/2008 | Seifert et al. |
| 2008/0108967 A1 | 5/2008 | Mizushima et al. |
| 2008/0132865 A1 | 6/2008 | Li et al. |
| 2008/0132872 A1 | 6/2008 | Trennepohl et al. |
| 2009/0197041 A1 | 8/2009 | Lake et al. |
| 2009/0247979 A1 | 10/2009 | Sosalla et al. |

* cited by examiner

PRINTED ABSORBENT ARTICLE COMPONENTS FOR A UNIFORM APPEARANCE

BACKGROUND

Absorbent products are often created from multiple materials and components that typically differ in look and feel. Real cloth underwear, however, is generally created from a single chassis material and waist and leg bands. As a result, the real cloth underwear has a consistent look and feel. With respect to disposable absorbent products made from multiple nonwoven components, consumers generally prefer products that more closely emulate the appearance of real cloth underwear. This desire leads to a need to reduce the actual differences in the appearance of a disposable absorbent across its different materials and components and to create perceptions of a similar look and feel across different materials.

Previous attempts in this area have focused on matching a solid color printed nonwoven with a pigmented nonwoven material, or by manufacturing what is typically referred to as a one-piece chassis.

SUMMARY

These problems can be addressed by using a method for manufacturing a disposable absorbent article having multiple components including selecting a first material appropriate for use as an outer cover; producing a chassis including the outer cover, the outer cover including an outer cover central region having an outer cover central region appearance; selecting a second material appropriate for use as an elastic panel, wherein the second material is different from the first material; and producing a first elastic panel having a first elastic panel central region. The method also includes printing the first elastic panel central region with a first elastic panel printed graphic; and attaching the first elastic panel to the chassis, wherein the selecting and printing are performed such that the first elastic panel central region gives the appearance of being substantially similar to the outer cover central region appearance.

In addition, a method for manufacturing a disposable absorbent article having a uniform garment-like appearance includes producing an assembly of at least a chassis having an outer cover and an elastic panel attached to the chassis, the assembly having a physical structure; and masking the physical structure of the assembly by printing the same graphic continuously on the outer cover and the elastic panel.

Further, a disposable absorbent article having a uniform garment-like appearance includes a chassis including an outer cover, a liner generally parallel to the outer cover, an absorbent core disposed therebetween, and an outer cover central region including an outer cover printed graphic; and a first elastic panel attached at a seam to the chassis, the first elastic panel including a first elastic panel central region having a first elastic panel central region appearance; wherein the outer cover includes a first material, wherein the first elastic panel includes a second material, wherein neither the outer cover central region nor the first elastic panel central region includes a printed waistband, and wherein the outer cover central region has the appearance of being substantially similar to the first elastic panel central region appearance.

Additionally, a disposable absorbent article having a uniform garment-like appearance includes a chassis including an outer cover, a liner generally parallel to the outer cover, and an absorbent core disposed therebetween; a first elastic panel attached at a seam to the chassis; and a second elastic panel attached at a seam to the chassis, wherein the first elastic panel is attached at a seam to the second elastic panel. The article also includes a waist opening and two leg openings; and a lateral circumference taken between the waist opening and the leg openings, wherein the outer cover includes a first material, wherein each elastic panel includes a second material, wherein the first material is different from the second material, and wherein the article includes a printed graphic along the entire circumference and on the outer cover.

Other features and aspects of the present disclosure are described in more detail below.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the appended figures in which.

Figure 1:
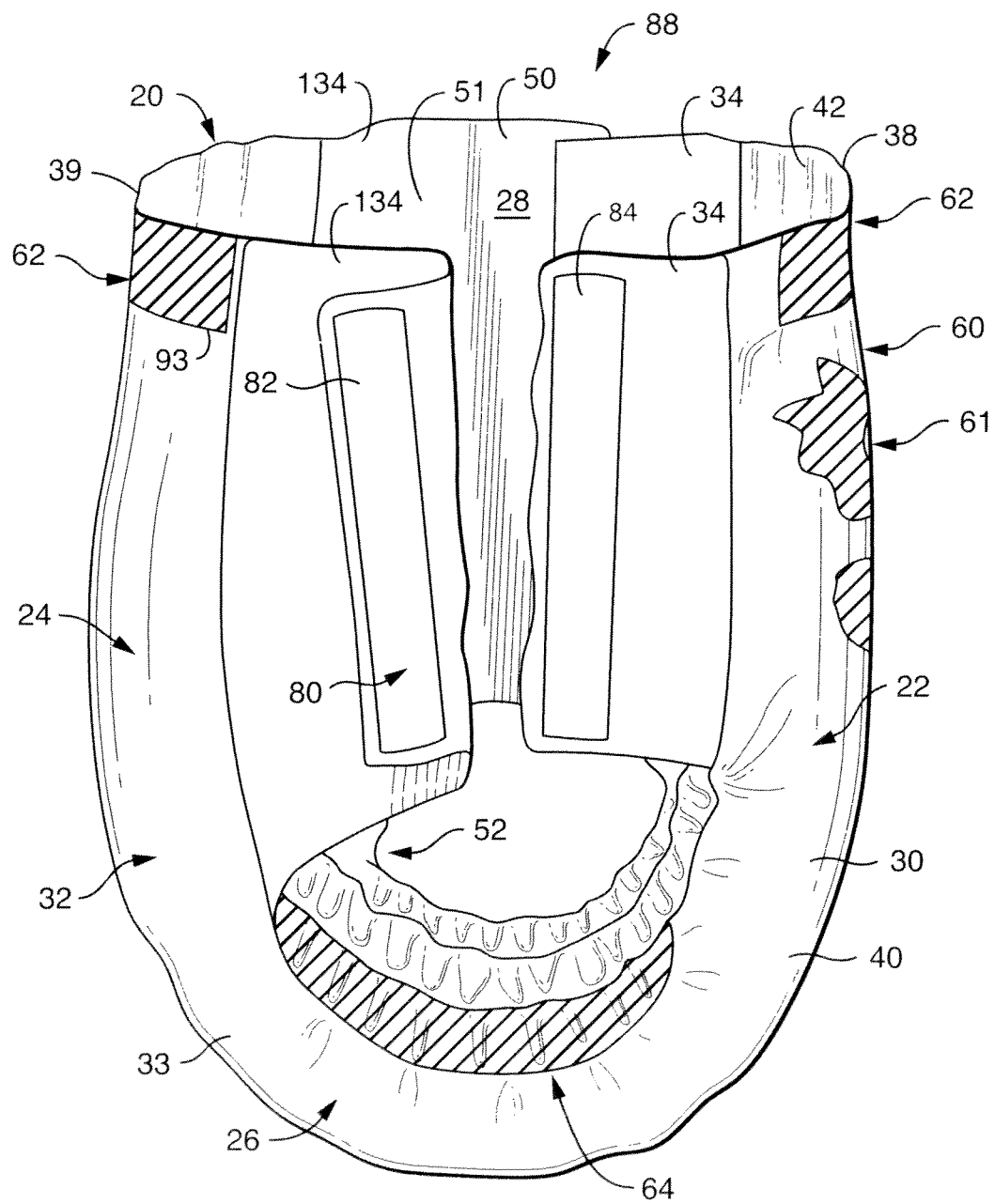
FIG. 1 is a side elevation of a child's pants with a fastening system of the pants shown connected on one side of the pants and disconnected on the other side of the pants.

Repeat use of reference characters in the present specification and drawings is intended to represent same or analogous features or elements of the disclosure.

DETAILED DESCRIPTION

As used herein, the terms "machine direction" or "MD" generally refers to the direction in which a material is produced. The term "cross-machine direction" or "CD" refers to the direction perpendicular to the machine direction.

As used herein the terms "extensible" or "extensibility" generally refers to a material that stretches or extends in the direction of an applied force by at least about 25%, in some aspects about 50%, and in some aspects, at least about 75% of its relaxed length or width. An extensible material does not necessarily have recovery properties. For example, an elastomeric material is an extensible material having recovery properties. A meltblown web can be extensible, but not have recovery properties, and thus, be an extensible, non-elastic material.

As used herein, the term "elastomeric" and "elastic" refers to a material that, upon application of a stretching force, is stretchable in at least one direction (such as the CD direction), and which upon release of the stretching force, contracts/returns to approximately its original dimension. For example, a stretched material can have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of not more than 1.25 inches. Desirably, the material contracts or recovers at least 50%, and even more desirably, at least 80% of the stretched length.

As used herein, the term "thermal point bonding" generally refers to a process performed, for example, by passing a material between a patterned roll (e.g., calender roll) and another roll (e.g., anvil roll), which may or may not be patterned. One or both of the rolls are typically heated.

As used herein, the term "breathability" generally refers to the water vapor transmission rate (WVTR) of an area of a material. Breathability is measured in grams of water per square meter per day (g/m$^2$/24 hours). The WVTR of a material can be measured in accordance with ASTM Standard E96-80. Alternatively, for materials having WVTR greater than about 3000 g/m$^2$/24 hours testing systems such as, for example, the PERMATRAN-W 100K water vapor permeation analysis system, commercially available from Modern Controls, Inc. (MOCON) of Minneapolis, Minn., can be used.

Reference now will be made in detail to various aspects of the disclosure, one or more examples of which are set forth below. Each example is provided by way of explanation, not limitation of the disclosure. In fact, it will be apparent to those skilled in the art that various modifications and variations can be made in the present disclosure without departing from the scope or spirit of the disclosure. For instance, features illustrated or described as part of one aspect, can be used on another aspect to yield a still further aspect. Thus, it is intended that the present disclosure cover such modifications and variations.

The methods and apparatus of the present disclosure can be used to make a variety of disposable absorbent articles such as disposable absorbent garments including diapers, training pants, feminine hygiene products, incontinence products, medical garments, other personal care or health care garments, swim pants, and the like. For ease of explanation, the methods and apparatus of the present disclosure are first described in connection with making child's pants, generally indicated as 20 in FIG. 1. In particular, the methods and apparatus will be described in terms of those for making pre-fastened disposable pants as described in U.S. patent application Ser. No. 09/444,083 titled "Absorbent Articles With Refastenable Side Seams" and filed Nov. 22, 1999 (corresponding to PCT application WO 00/37009 published Jun. 29, 2000) by A. L. Fletcher et al., the disclosure of which is incorporated herein by reference. Pants 20 can also be constructed using the methods and apparatus disclosed in U.S. Pat. No. 4,940,464 issued Jul. 10, 1990 to Van Gompel et al.; and U.S. Pat. No. 5,766,389 issued Jun. 16, 1998 to Brandon et al.; the disclosures of which are also incorporated herein by reference.

The methods and apparatus of the present disclosure are thereafter further described in connection with making an adult pant, generally indicated at 220 in FIGS. 4 and 5.

It should be understood that as used herein, the term "component" includes not only discrete objects, but also objects yet to be formed into discrete objects (e.g., objects yet to be severed into discrete objects from a continuous sheet or web of material), particles (e.g., superabsorbent particles or polymers), adhesives, lotions, ointments, and other substances, as well as portions or characteristics of any such components including, for example, fold lines, bond lines (e.g., ultrasonic bond lines), bonded or adhered regions, and registration marks applied to or about components for subsequent detection during a manufacturing or inspection process.

With reference now to the drawings, and in particular to FIG. 1, a pair of pants 20 is illustrated in a partially fastened condition and include an absorbent chassis 32 having a front waist region 22, a back waist region 24, a crotch region 26 interconnecting the front and back waist regions, an inner surface 28 which is configured to contact the wearer, and an outer surface 30 opposite the inner surface and configured to contact the wearer's clothing. With additional reference to FIGS. 2 and 3, the absorbent chassis 32 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 2:
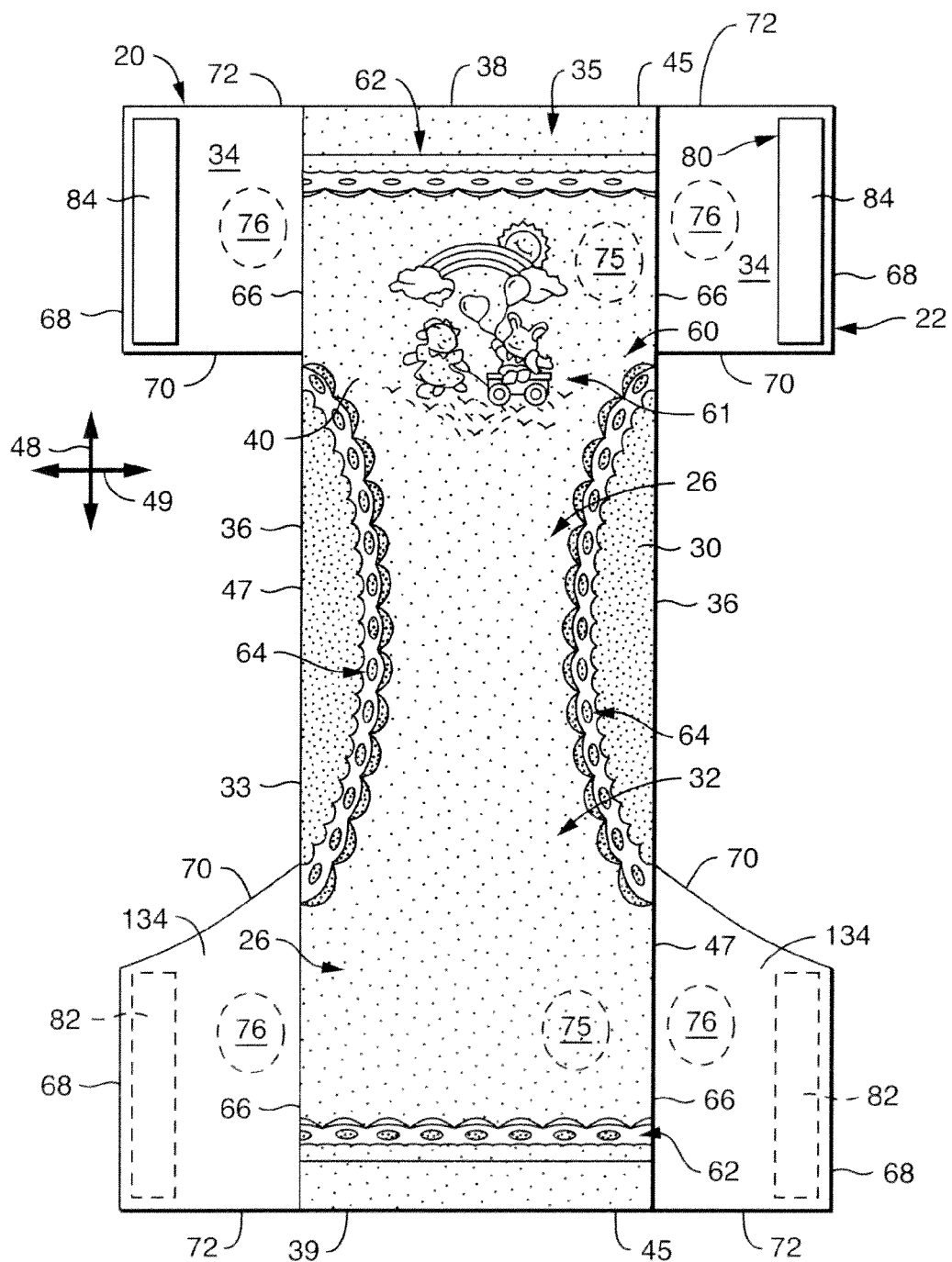
FIG. 2 is a bottom plan view of the pants of FIG. 1 in an unfastened, stretched and laid flat condition to show the surface of the pants which faces away from the wearer.

The illustrated absorbent chassis 32 includes a composite structure 33 (FIGS. 2 and 3), which when laid flat can be rectangular or any other desired shape, and has a pair of laterally opposite front side panels 34 and a pair of laterally opposite back side panels 134 extending outward therefrom. Each side panel 34, 134 includes a side panel central region 76 positioned generally on each side panel 34, 134, and does not include a waistband or leg bands (FIG. 2). The side panel central region 76 has a side panel central region appearance, which is the physical appearance of the side panel central region 76.

Figure 3:
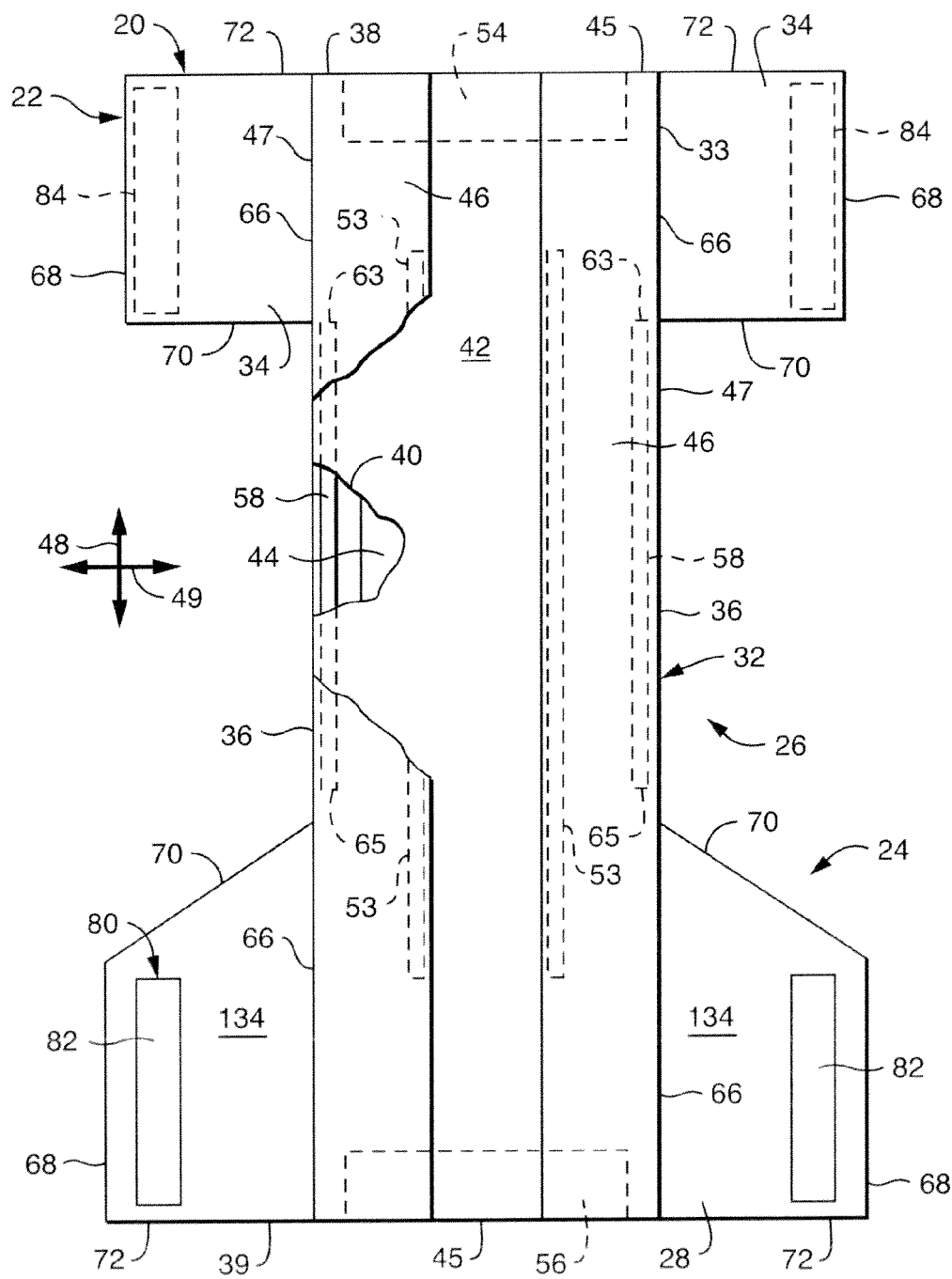
FIG. 3 is a top plan view of the pants in its unfastened, stretched and laid flat condition to show the surface of the pants which faces the wearer when the pants are worn, with portions of the pants being cut away to reveal underlying features.

The composite structure 33 and side panels 34, 134 can include two or more separate elements, as shown in FIG. 1, or be integrally formed. Integrally formed side panels 34, 134 and composite structure 33 would include at least some common materials, such as the bodyside liner, flap composite, outer cover, other materials and/or combinations thereof, and could define a one-piece elastic, stretchable, or non-stretchable pants. The illustrated composite structure 33 includes an outer cover 40, a bodyside liner 42 (FIGS. 1 and 3) connected to the outer cover in a superposed relation, an absorbent assembly 44 (FIG. 3) disposed between the outer cover and the bodyside liner, and a pair of containment flaps 46 (FIG. 3). The illustrated composite structure 33 has opposite ends 45 (FIGS. 2 and 3) that form portions of the front and back waist edges 38 and 39, and opposite side edges 47 which form portions of the side edges 36 of the absorbent chassis 32 (FIGS. 2 and 3). The outer cover 40 includes an outer cover central region 75 positioned generally in the front and/or back waist regions 22, 24, and does not include a waistband or leg bands (FIG. 2). The outer cover central region 75 has an outer cover central region appearance, which is the physical appearance of the outer cover central region 75.

For reference, arrows 48 and 49 (FIGS. 2 and 3) depict the orientation of the longitudinal axis and the transverse or lateral axis, respectively, of the pants 20.

With the pants 20 in the fastened position as partially illustrated in FIG. 1, the front and back side panels 34, 134 are connected together by a fastening system 80 to define a three-dimensional pants configuration having an interior space 51, a waist opening 50 for receiving the wearer into the interior space of the pants, a pair of leg openings 52 and engagement seams 88 along which the side panels 34, 134 are connected. The interior space 51 of the pants 20 is thus bounded by the absorbent chassis 32, the engagement seams 88 and the portions of the side panels 34, 134 extending on opposite sides of the engagement seams 88 (e.g., between the engagement seams 88 and the absorbent chassis 32). As used herein, the "interior space" 51 is intended to refer to the space between any two portions of a three-dimensional article which generally oppose each other. It is understood that a transverse cross-section of the article need not be closed, e.g., continuous, to define the interior space 51. For example, a twodimensional article can be generally folded over on itself so that two portions of the article oppose each other to define an interior space of the article therebetween. Thus, the interior space 51 of the pants 20 shown in FIG. 1 can be defined by the side panels 34, 134 themselves or, if the side panels 34, 134 are fully straightened therebetween, the interior space is defined by a combination of the side panels 34, 134 and the front and back waist regions 22, 24 of the absorbent chassis 32.

The front waist region 22 includes the portion of the pants 20 which, when worn, is positioned on the front of the wearer while the back waist region 24 includes the portion of the pants which, when worn, is positioned on the back of the wearer. The crotch region 26 of the pants 20 includes the portion of the pants 20 which, when worn, is positioned between the legs of the wearer and covers the lower torso of the wearer. The front and back side panels 34 and 134 include the portions of the pants 20 which, when worn, are positioned on the hips of the wearer. The waist edges 38 and 39 of the absorbent chassis 32 are configured to encircle the waist of the wearer when worn and together define the waist opening 50 (FIG. 1). Portions of the side edges 36 in the crotch region 26 generally define the leg openings 52.

The absorbent chassis 32 is configured to contain and/or absorb any exudates discharged from the wearer. For example, the absorbent chassis 32 desirably although not necessarily includes the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright configuration in at least the crotch region 26 of the pants 20 to form a seal against the wearer's body. The containment flaps 46 can be located along the side edges 36 of the absorbent chassis 32, and can extend longitudinally along the entire length of the absorbent chassis 32, or can only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the pants 20 desirably although not necessarily include a front waist elastic member 54, a back waist elastic member 56, and leg elastic members 58, as are known to those skilled in the art (FIG. 3). The waist elastic members 54 and 56 can be operatively joined to the outer cover 40 and/or the bodyside liner 42 along the opposite waist edges 38 and 39, and can extend over part or all of the waist edges. The leg elastic members 58 can be operatively joined to the outer cover 40 and/or the bodyside liner 42 along the opposite side edges 36 and positioned in the crotch region 26 of the pants 20. The leg elastic members 58 can be longitudinally aligned along each side edge 47 of the composite structure 33. Each leg elastic member 58 has a front terminal point 63 and a back terminal point 65, which represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

As shown in FIGS. 1 and 2, the pants 20 and in particular the outer cover 40 desirably includes one or more appearance-related components. Examples of appearance-related components include, but are not limited to, graphics; highlighting or emphasizing leg and waist openings in order to make product shaping more evident or visible to the user; highlighting or emphasizing areas of the product to simulate functional components such as elastic leg bands, elastic waistbands, simulated "fly openings" for boys, ruffles for girls; highlighting areas of the product to change the appearance of the size of the product; registering wetness indicators, temperature indicators, and the like in the product; registering a back label, or a front label, in the product; and registering written instructions at a desired location in the product.

The illustrated pair of pants 20 is designed for use by young girls and includes a registered outer cover graphic 60 (FIGS. 1 and 2). In this design, the registered graphic 60 includes a primary pictorial image 61, simulated waist ruffles 62, and simulated leg ruffles 64. The primary pictorial image 61 includes an object graphic such as a rainbow, sun, clouds, animal characters, wagon and balloons. Any suitable design can be utilized for pants intended for use by young girls, so as to be aesthetically and/or functionally pleasing to them and the caregiver. The appearance-related components are desirably positioned on the pants 20 at selected locations, which can be carried out using the methods disclosed in U.S. Pat. No. 5,766,389 issued Jun. 16, 1998 to Brandon et al., the entire disclosure of which is incorporated herein by reference. The primary pictorial image 61 is desirably positioned in the front waist region 22 along the longitudinal center line of the pants 20.

The printed graphics on the pants 20 can share a color palette, can be of the same color, can be of complementary colors, or can follow any suitable color scheme. Different areas of the pants 20 can also be printed with similar or identical graphical elements such as stars, circles, butterflies, etc. Different areas of the pants 20 can also be printed with similar or identical graphics that share a graphic theme. For example, the pants 20 can be printed with flowers that might or might not be identical in size, type, color, etc., but that all share the flower theme. In another aspect, the article can be reverse printed such that graphical elements, for example, appear as an absence of printing.

As noted previously, the illustrated pants 20 have front and back side panels 34 and 134 disposed on each side of the absorbent chassis 32. The front side panels 34 can be permanently bonded along seams 66 to the composite structure 33 of the absorbent chassis 32 in the respective front and back waist regions 22 and 24. More particularly, as seen best in FIGS. 2 and 3, the front side panels 34 can be permanently bonded to and extend transversely outward beyond the side edges 47 of the composite structure 33 in the front waist region 22, and the back side panels 134 can be permanently bonded to and extend transversely outward beyond the side edges of the composite structure in the back waist region 24. The side panels 34 and 134 can be bonded to the composite structure 33 using attachment means known to those skilled in the art such as adhesive, thermal or ultrasonic bonding. Alternatively, the side panels 34 and 134 can be formed as an integral portion of a component of the composite structure 33. For example, the side panels can include a generally wider portion of the outer cover 40, the bodyside liner 42, and/or another component of the absorbent chassis 32. The front and back side panels 34 and 134 can be permanently bonded together or be releasably connected with one another such as by the fastening system 80 of the illustrated aspect.

As best illustrated in FIGS. 2 and 3, the front and back side panels 34, 134 each have an outer edge 68 spaced laterally from the seam 66, a leg end edge 70 disposed toward the longitudinal center of the pants 20, and a waist end edge 72 disposed toward a longitudinal end of the pants. The leg end edge 70 and waist end edge 72 extend from the side edges 47 of the composite structure 33 to the outer edges 68. The leg end edges 70 of the side panels 34 and 134 form part of the side edges 36 of the absorbent chassis 32. In the back waist region 24, the leg end edges 70 are desirably although not necessarily curved and/or angled relative to the transverse axis 49 to provide greater coverage toward the back of the pants 20 as compared to the front of the pants. The waist end edges 72 are desirably parallel to the transverse axis 49. The waist end edges 72 of the front side panels 34 form part of the front waist edge 38 of the absorbent chassis 32, and the waist end edges 72 of the back side panels 134 form part of the back waist edge 39 of the absorbent chassis 32.

In particular aspects for improved fit and appearance, the side panels 34, 134 desirably have an average length measured parallel to the longitudinal axis 48 which is about 15 percent or greater, and particularly about 25 percent or greater, of the overall length of the pants, also measured parallel to the longitudinal axis 48. For example, in pants 20 having an overall length of about 54 centimeters, the side panels 34, 134 desirably have an average length of about 10 centimeters or greater, such as about 15 centimeters. While each of the side panels 34, 134 extends from the waist opening 50 to one of the leg openings 52, the illustrated back side panels 134 have a continually decreasing length dimension moving from the seam 66 to the outer edge 68, as is best shown in FIGS. 2 and 3.

Each of the side panels 34, 134 can include one or more individual, distinct pieces of material. In particular aspects, for example, each side panel 34, 134 can include first and second side panel portions that are joined at a seam, or can include a single piece of material which is folded over upon itself (not shown).

The side panels 34, 134 desirably although not necessarily include an elastic material capable of stretching in a direction generally parallel to the transverse axis 49 of the pants 20. Suitable elastic materials, as well as one process of incorporating elastic side panels into pants, are described in the following U.S. Pat. No. 4,940,464 issued Jul. 10, 1990 to Van Compel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. An alternative elastic material is described below. In particular aspects, the elastic material includes a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material can include other woven or nonwoven materials, such as those described above as being suitable for the outer cover 40 or bodyside liner 42; mechanically pre-strained composites; or stretchable but inelastic materials.

The methods and apparatus of the present disclosure are further described in connection with an adult pant, generally indicated at 220 in FIGS. 4 and 5. Referring to FIG. 4, which illustrates exemplary aspects of the present disclosure, a pant-like disposable absorbent garment includes a front panel 222, the front panel 222 defining a front waist edge 223, first and second front leg edges 221, opposing first and second front side edges 224 and 225 that extend from the front waist edge 223 to the first and second front leg edges 221, and a front panel width 234 that extends from the first front side edge 224 to the second front side edge 225 (as measured at the front waist edge when the product is in a laid-flat, open, and fully extended configuration).

The garment further includes a back panel 226, the back panel 226 defining a back waist edge 227, first and second back leg edges 245, opposing first and second back side edges 228 and 229 that extend from the back waist edge 227 to the first and second back leg edges 245, and a back panel width 244 that extends from the first back side edge 228 to the second back side edge 229 (as measured at the back waist edge when the product is in a laid-flat, open and fully extended configuration). The front panel 222 and the back panel 226 each include an elastic panel central region 276 positioned generally on each front and back panel 222, 226, and does not include a waistband or leg bands (FIG. 4). The elastic panel central region 276 has an elastic panel central region appearance, which is the physical appearance of the elastic panel central region 276.

Figure 4:
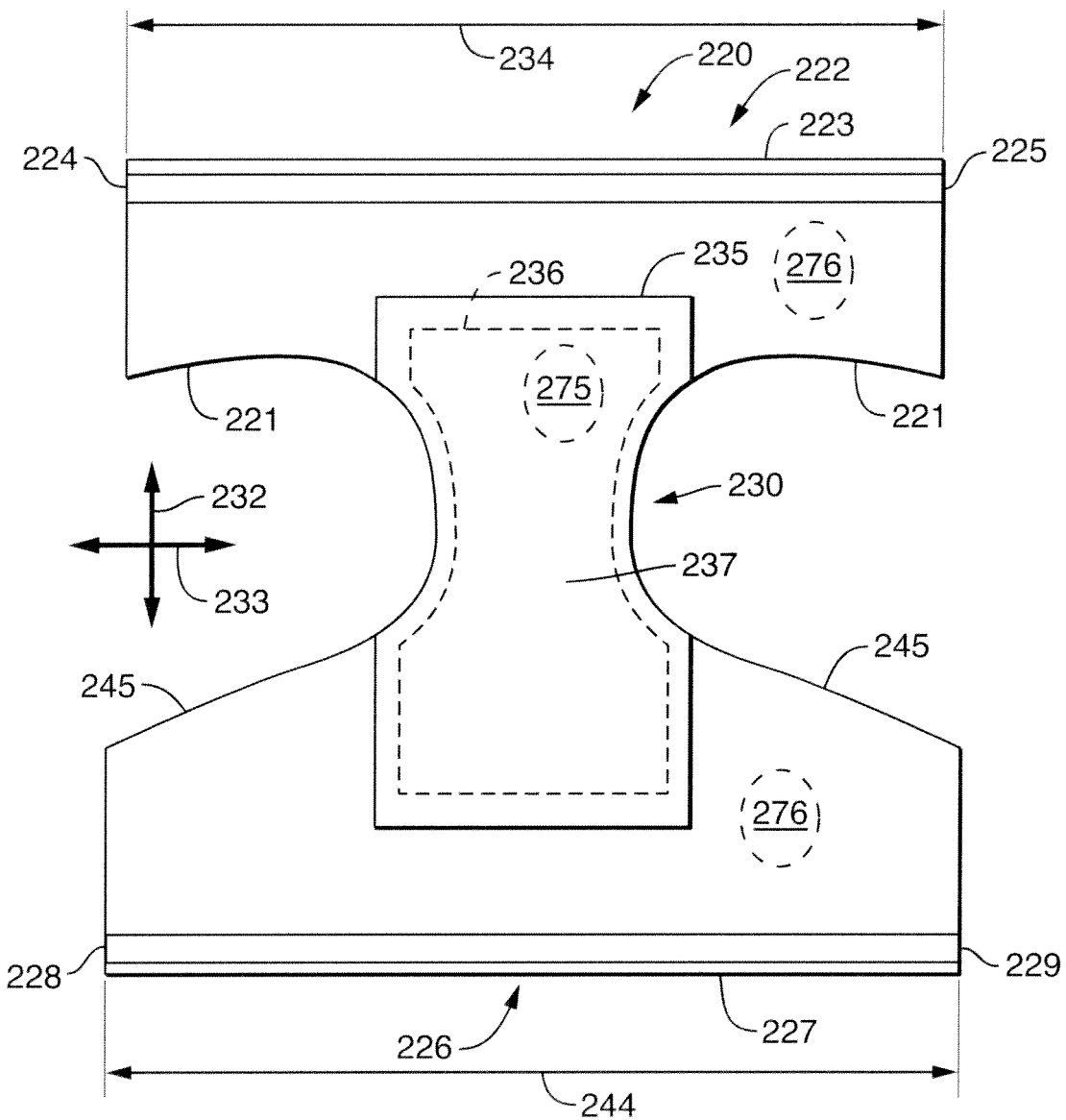
FIG. 4 representatively illustrates a plan view of one aspect of an absorbent garment in a longitudinally-stretched and laid-flat condition, prior to the joining of the front and back waist regions, and showing the surface of the article that faces the wearer when the article is worn, and with portions cut away to show underlying features.
Figure 5:
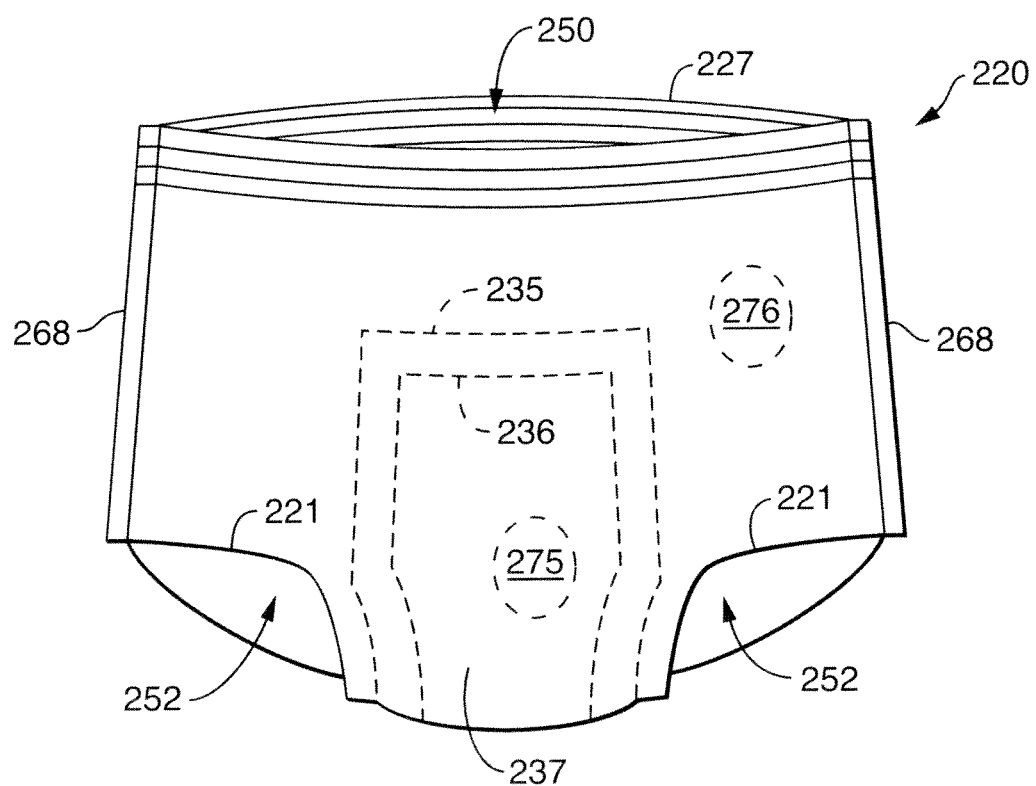
FIG. 5 representatively illustrates the garment of FIG. 4 in a closed condition.

In one aspect, the garment further includes a crotch panel 230 positioned longitudinally between the front panel 222 and the back panel 226, wherein the front panel 222, the back panel 226, and the crotch panel 230 are continuous and integral with each other, as representatively illustrated in FIGS. 4 and 5. One version of such an aspect includes an hourglass-shaped panel having an elastomeric film laminate. In particular aspects, the laminate includes two nonwoven layers superposed on opposing top and bottom surfaces of an elastomeric polymeric film such that the polymeric film is sandwiched between the two nonwoven facings, wherein both the polymeric film and both nonwoven layers extend substantially through the entire area of each laminate. Another version of such an aspect includes providing an hourglass panel including a nonwoven substrate that is imparted with elastic properties by adhesively attaching elastic strands thereto. The strands and adhesive are, in particular aspects, sandwiched to the hourglass panel with a second nonwoven layer or layers.

The garment further includes an absorbent insert 235. The insert includes an absorbent member 236. One example of a suitable insert 235 includes a liquid-permeable bodyside liner, a garment-side liquid-impermeable backsheet 237, and an absorbent member 236 included of wood pulp fluff and superabsorbent polymer. Each absorbent insert 235 is attached to an hourglass-shaped panel. The absorbent insert is attached to and extends between the front panel 222 and the back panel 226 (FIG. 4). The backsheet 237 includes an outer cover central region 275 positioned generally on the backsheet 237, and does not include a waistband or leg bands (FIG. 4). The outer cover central region 275 has an outer cover central region appearance, which is the physical appearance of the outer cover central region 275.

As illustrated in FIG. 4, the garment defines a longitudinal direction 232 that extends between the front waist edge 223 and the back waist edge 227, and a transverse direction 233 that is perpendicular to the longitudinal direction 232 and that extends between the first front side edge 224 and the second front side edge (and between the first back side edge 228 and the second back side edge 229).

In particular aspects shown in FIG. 5, side seams 268 of the garment 220 are permanently bonded, non-refastenable side seams. For example, the joining of the first and second front side edges to the first and second back side edges creates a pair of permanently bonded, non-refastenable side seams. In other aspects, the side seams 268 are releasable and refastenable. For example, the joining of the first and second front side edges to the first and second back side edges creates a pair of releasable and refastenable seams. The closed article as shown in FIG. 6 includes a waist opening 250 and a pair of leg openings 252.

In particular aspects of the present disclosure, the front panel defines a front crotch edge longitudinally opposite the front waist edge, and the back panel defines a back crotch edge longitudinally opposite the back waist edge, and the front crotch edge is longitudinally spaced apart from the back crotch edge such that the front panel and the back panel are separate from and non-integral with each other.

It is apparent that the disposable absorbent articles described herein share similar features, even though such features are conventionally labeled differently for different types of products. The present disclosure is intended to apply to any product described herein. For example, subject matter using the term "side panel" is intended to be equally applicable to the body panel of an adult care product and to the more generic terms elastic panel and stretchable panel. Subject matter using the term "chassis" is intended to be equally applicable to the absorbent insert of an adult care product. Subject matter using the term "outer cover" is intended to be equally applicable to the backsheet of an adult care product. Leg openings, waist openings, waist edges, waistbands, and leg bands are similar for all products. Other similarities and equivalencies will be apparent to those skilled in the art.

In one aspect of the present disclosure, the elastic panels can be constructed from an elastic laminate that is a composite that includes an elastic film laminated to a meltblown facing. By replacing VFL elastic panels with a new elastic laminate material described herein on baby, child, and youth pants and replacing the stranded chassis with the new material described herein on adult pants, one-piece garment-like look can be achieved while maintaining the high stretch properties required to fit the user.

The smoothness or texture quality of a retracted elastic laminate can be quantified through relatively simple physical measurements. For a laminate having a cross section defined by the y-z plane, where the material is elastically functional along the y axis, and the x-y plane defines the printable surface of the laminate, the corrugations formed by the retracted facing in the y-z plane have descriptive values similar to those of a wave. Whereas a wave has a frequency, wavelength, and amplitude, the corrugations of the facings have a corrugation density, a corrugation spacing, and a corrugation height. It is both the magnitude and variability of these values that determine the resulting smoothness or texture of the material.

The regularity of the corrugation height determines the uniformity and thus smoothness of the retracted surface. For a laminate having a cross section in the y-z plane, and a printable surface in the x-y plane, the regularity of corrugation height measured on the z axis determines the consistency of laminate look and feel. A perfectly-consistent corrugation height wave to wave yields the same contact length at the crest of each wave. For the elastic laminate described herein, the corrugation height standard deviation varies from 120 to 190 micrometers versus a standard deviation range of 240-410 micrometers for VFL, as much as a 200% advantage. The magnitude of corrugation density determines the surface area available on the elastic laminate. The greater the area available the smoother the material will look and feel. With retracted laminates, look and feel is primarily accomplished at the crest of the corrugation wave. The higher the corrugation density, the more facings area at the laminate surface that is available. The elastic laminates described herein possess 1.4-2.0 corrugations per linear mm compared to 0.7-1.10 corrugations per linear mm for VFL and 0.7 corrugations per linear mm for LYCRA-brand synthetic fiber laminate, which yields as much as a 200% advantage in smooth surface area. A corrugation density of greater than 1.2 corrugations per liner mm is preferable to satisfactorily match the appearance of a non-elastic printed surface such as SFL. It should be noted that corrugation density and corrugation spacing are simply different representations of the same physical data.

Further, for an elastic laminate of the present disclosure, adjacent cross sections have corrugation spacing standard deviations of 165 micrometers and 187 micrometers for average corrugation spacings of 670 micrometers and 714 micrometers respectively, while VFL has corrugation spacing standard deviations of 230 micrometers and 410 micrometers for average corrugation spacings of 1215 micrometers and 1560 micrometers respectively. The laminate of the present disclosure has a variation in variability from plane to plane of less than 15% while VFL has a variation in variability from plane to plane is greater than 75%.

Elastic laminate of the present disclosure also possesses a corrugation height range of 385-521 micrometers compared to 826-1552 micrometers for VFL and 1680 micrometers for LYCRA-brand synthetic fiber laminate, resulting in as much as a 300% advantage. A corrugation height of less than 700 micrometers is preferred to satisfactorily maintain quality across the performance range of an elastic laminate fit for use in an elastic panel application.

It should be noted that the magnitude of the wave values for the elastic laminate of the present disclosure on average are approximately half that of VFL or LYCRA-brand synthetic fiber laminate. This is not a coincidence. The fundamental construction of an elastic laminate of the present disclosure is completely unique. VFL and LYCRA-brand synthetic fiber laminate are constructed using a spray-on or sure-wrap glue that results in a significant amount of SB to SB bonding in the spaces between strands. Conversely, the elastic laminate of the present disclosure has zero SB to SB bonding of any type. As a result, when VFL or LYCRA-brand synthetic fiber laminate retract, the bonded facings between strands reacts as a single mat of material, creating one large-scale continuous corrugation between the strand and random small scale corrugations at the strand surface. This results in large absolute wave values in the cross section between the strands and large wave value variations in the planes between the strands versus through the strands. Conversely, facings of the elastic laminate of the present disclosure form corrugations that are mirrored about the y axis, and hence have by definition wave values (and subsequent standard deviations) of at least half that of a VFL of comparable range. In addition, because the mechanical bonding of the elastic laminate of the present disclosure is exact when compared to the random disposition of bond points resulting from glue lamination, the variation of the wave values tends to be even less than would be expected as a result of the reduction in absolute magnitudes alone.

Lamination of the elastic laminate is accomplished via a patterned bonding technique (e.g., thermal point bonding, ultrasonic bonding, etc.) in which the materials are supplied to a nip defined by at least one patterned roll. Through selective control of certain parameters of the lamination process, such as film content, bonding pattern, degree of film tension, bonding conditions, etc., the durability of the meltblown facing can be improved. During lamination, for example, apertures and discrete bond sites can be concurrently formed in the elastic film. The discrete bond sites can be located proximate (adjacent or near to) a perimeter defined by corresponding apertures formed by displacement of the film. The location of the bond sites adjacent to or near the apertures can enhance the durability of the meltblown facing by strengthening the area surrounding the apertures. Furthermore, the polymer content of the elastic film and the temperature/pressure of lamination can be selected so that the film possesses a sufficient tack for adhering to the facing at regions other than those fused together by the bonding elements of the patterned roll. Such secondary bonding further stabilizes the meltblown facing and renders it suitable for printing.

Other aspects of the lamination technique of the present disclosure can also help provide a surface of the meltblown facing that is suitable for printing. For example, the film is under tension in the machine direction during lamination. Subsequent to lamination, however, the film is retracted so that the facing retracts toward its original machine direction length, thereby gathering and forming pleats. When formed according to the present disclosure, it has been discovered that these pleats have a relatively small amplitude (height), as well as a substantially uniform frequency across the surface of the facing. Such a small height and increased regularity improves the ability to transfer an ink to the "peaks" of the pleats, thereby improving the print quality and uniformity.

The elastic film of the present disclosure is formed from one or more elastomeric polymers that are melt-processible, i.e., thermoplastic. Any of a variety of thermoplastic elastomeric polymers can generally be employed in the present disclosure, such as elastomeric polyesters, elastomeric polyurethanes, elastomeric polyamides, elastomeric copolymers, elastomeric polyolefins, and so forth. In one particular aspect, elastomeric semi-crystalline polyolefins are employed due to their unique combination of mechanical and elastomeric properties. That is, the mechanical properties of such semi-crystalline polyolefins allows for the formation of films that readily aperture during thermal bonding, but yet retain their elasticity.

Besides polymers, the elastic film of the present disclosure can also contain other components as is known in the art. In one aspect, for example, the elastic film contains a filler. Fillers are particulates or other forms of material that can be added to the film polymer extrusion blend and that will not chemically interfere with the extruded film, but which can be uniformly dispersed throughout the film. Fillers can serve a variety of purposes, including enhancing film opacity and/or breathability (i.e., vapor-permeable and substantially liquid-impermeable). For instance, filled films can be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes.

Other additives can also be incorporated into the film, such as melt stabilizers, processing stabilizers, heat stabilizers, light stabilizers, antioxidants, heat aging stabilizers, whitening agents, antiblocking agents, bonding agents, tackifiers, viscosity modifiers, etc.

The elastic film of the present disclosure can be mono- or multi-layered. Multilayer films can be prepared by co-extrusion of the layers, extrusion coating, or by any conventional layering process. Such multilayer films normally contain at least one base layer and at least one skin layer, but can contain any number of layers desired. The thickness of the skin layer(s) is generally selected so as not to substantially impair the elastomeric properties of the film. The properties of the resulting film can generally vary as desired.

Generally speaking, the facing used in the composite contains a meltblown web to improve the receptiveness of the facing to an ink. Namely, meltblown webs generally have small pores that allow the ink to exhibit better surface retention upon printing. The small pore size can also provide other benefits, such as inhibiting the passage of liquids and particles, while allowing gases (e.g., air and water vapor) to pass therethrough.

The meltblown web is typically formed from a polymer having a softening temperature that is higher than the temperature imparted during bonding. In this manner, the polymer does typically not soften to such an extent that the fibers of the meltblown web become completely melt flowable and unable to form bonds. If desired, biodegradable polymers, such as those described above, can also be employed. Synthetic or natural cellulosic polymers can also be used. It should be noted that the polymer(s) can also contain other additives, such as processing aids or treatment compositions to impart desired properties to the fibers, residual amounts of solvents, pigments or colorants, and so forth.

Monocomponent and/or multicomponent fibers can be used to form the meltblown web. Monocomponent fibers are generally formed from a polymer or blend of polymers extruded from a single extruder. Multicomponent fibers are generally formed from two or more polymers (e.g., bicomponent fibers) extruded from separate extruders. The polymers can be arranged in substantially constantly positioned distinct zones across the cross-section of the fibers. The components can be arranged in any desired configuration, such as sheath-core, side-by-side, pie, island-in-the-sea, three island, bull's eye, or various other arrangements known in the art.

The desired denier of the fibers can vary depending on the desired application.

Although not required, the meltblown web can optionally be bonded using any conventional technique, such as with an adhesive or autogenously (e.g., fusion and/or self-adhesion of the fibers without an applied external adhesive). Suitable autogenous bonding techniques can include ultrasonic bonding, thermal bonding, through-air bonding, calender bonding, and so forth. As is well known to those skilled in the art, the temperature and pressure required can vary depending upon many factors including but not limited to, pattern bond area, polymer properties, fiber properties and nonwoven properties. The meltblown web can also be necked in one or more directions prior to lamination to the film of the present disclosure.

If desired, the meltblown facing can have a multi-layer structure. Suitable multi-layered facings can include, for instance, spunbond/meltblown/spunbond (SMS) laminates and spunbond/meltblown (SM) laminates.

The meltblown facing can also contain an additional fibrous component such that it is considered a composite. For example, a meltblown web can be entangled with another fibrous component using any of a variety of entanglement techniques known in the art (e.g., hydraulic, air, mechanical, etc.). In one particular aspect, the facing can be a "coform web" made by a process in which at least one meltblown die head is arranged near a chute through which other materials are added to the web while it is forming.

Regardless of its particular construction, one particular benefit of the present disclosure is that the meltblown facing can have a relatively low basis weight and yet remain durable and still present a suitable surface for printing. Such a low basis weight can provide a variety of benefits, including reduced costs and improved flexibility.

In addition to an elastic film and meltblown facing, the composite of the present disclosure can also include other facings as is known in the art. For example, the composite can include an additional nonwoven facing, such as a meltblown web, spunbond web, bonded carded web, wet-laid web, airlaid web, coform web, hydraulically entangled web, etc. The additional facing(s) can be multi-layered and/or a composite material, such as described above.

Lamination is accomplished via a patterned bonding technique (e.g., thermal point bonding, ultrasonic bonding, etc.) in which the materials are supplied to a nip defined by at least one patterned roll. Thermal point bonding, for instance, typically employs a nip formed between two rolls, at least one of which is patterned. Ultrasonic bonding, on the other hand, typically employs a nip formed between a sonic horn and a patterned roll. Regardless of the technique chosen, the patterned roll contains a plurality of raised bonding elements to bond the film to the meltblown facing.

As indicated above, the durability and stability of the meltblown facing is enhanced by the concurrent formation of apertures and discrete bond sites during lamination. Such apertures can also provide a desired level of texture, softness, hand feel, and/or aesthetic appeal to the composite without having a significant adverse effect on its elastic properties. Aperture and bond formation are accomplished in the present disclosure by selectively controlling certain parameters of the lamination process, such as film content, bonding pattern, degree of film tension, bonding conditions, etc. The size of the bonding elements, for example, can be specifically tailored to facilitate the formation of apertures in the film and enhance bonding between the film and the meltblown facing.

Besides the size of the bonding elements, the overall bonding pattern can also be selectively controlled to achieve the desired aperture formation. In this manner, the bonding elements will present a relatively large surface to the film in a direction substantially perpendicular to that which the film moves. This increases the area over which shear stress is imparted to the film and, in turn, facilitates aperture formation.

The pattern of the bonding elements is generally selected so that the nonwoven composite has a total bond area of less than about 50% (as determined by conventional optical microscopic methods), and in some aspects, less than about 30%.

The selection of an appropriate bonding temperature (e.g., the temperature of a heated roll) will help melt and soften the low-softening point elastomeric polymer(s) of the film at regions adjacent to the bonding elements. The softened elastomeric polymer(s) can then flow and become displaced during bonding, such as by pressure exerted by the bonding elements. The displaced portions of the film surrounding the apertures can also fuse to the meltblown facing, thereby forming an integral nonwoven composite. Furthermore, because the elastomeric polymer(s) can physically entrap or adhere to the fibers at the bond sites, adequate bond formation can be achieved without requiring substantial softening of the polymer(s) used to form the meltblown facing. Thus, the meltblown facing remains substantially unbonded to the film or other materials at those regions located directly adjacent to (e.g. above or below) the apertures. Further, the meltblown facing is also generally unapertured, although it can of course develop some small cuts or tears during processing.

To achieve such concurrent aperture and bond formation without substantially softening the polymer(s) of the meltblown facing, the bonding temperature and pressure can be selectively controlled. Likewise, the pressure exerted by rolls ("nip pressure") during thermal bonding can be varied. Of course, the residence time of the materials can influence the particular bonding parameters employed.

Another factor that influences concurrent aperture and bond formation is the degree of tension in the film during lamination. An increase in film tension, for example, typically correlates to an increase in aperture size. Of course, a film tension that is too high can adversely affect the integrity of the film.

The film can be "pre-stretched" (prior to lamination) by rolls rotating at different speeds of rotation so that the sheet is stretched to the desired stretch ratio in the machine direction. This uniaxially stretched film can also be oriented in the cross-machine direction to form a "biaxially stretched" film. The orientation temperature profile during the "pre-stretching" operation is generally below the melting point of one or more polymers in the film, but high enough to enable the composition to be drawn or stretched. When "pre-stretched" in the manner described above, the degree of stretch during lamination can be increased, maintained, or slightly reduced (retracted) to desired degree of tension.

Upon lamination, the elastic film is bonded to the meltblown facing and apertured. The size and/or pattern of the resulting apertures generally correspond to the size and/or pattern of the bonding elements. That is, the apertures can have a length, width, aspect ratio, and orientation as described above. Similarly, the longitudinal axis of one or more of the apertures (longest dimension along a center line of the aperture) can be skewed relative to the machine direction of the elastic film.

Upon formation, the elastic film can retract toward its original machine direction length and become shorter in the machine direction, thereby forming "pleats" in the meltblown facing. The resulting elastic composite thus becomes extensible in the machine direction to the extent that the pleats in the facing can be pulled back out flat, thereby allowing the elastic film to elongate.

Generally speaking, the resulting "pleats" in the meltblown facing have a relatively small amplitude (height) and wavelength ("peak-to-peak" distance), thereby rending the surface more suitable for printing. It is believed that pleats having a small height and wavelength (high density) can improve print quality by providing a larger effective surface area for transfer of the ink.

Further detail with respect to elastic laminates of the present disclosure can be found in co-pending U.S. Patent Publication No. 2008/0095978 entitled "Nonwoven Composite Containing An Apertured Elastic Film," and in co-pending U.S. patent application Ser. No. 12/580,847, entitled "Matching Absorbent Article Components For A Uniform Appearance," which are incorporated herein by reference to the extent they do not conflict herewith.

Materials and processes suitable for forming such absorbent articles are well known to those skilled in the art. Absorbent articles can include, for example, a substantially liquid-impermeable layer (e.g., outer cover), a liquid-permeable layer (e.g., bodyside liner, surge layer, etc.), and an absorbent core. In one particular aspect of the present disclosure, the printed nonwoven composite can be used to form a substantially liquid-impermeable layer (e.g., outer cover) of the absorbent article. In another aspect, the printed nonwoven composite of the present disclosure can be used to form a liquid-permeable layer (e.g., bodyside liner, surge layer) of the absorbent article.

Returning to FIGS. 1-3, pants 20 can have the side panels 34, 134 affixed to each other for securing the pants 20 about the waist of the wearer. The side panels 34, 134 can be affixed by bonding, mechanical fasteners, or any other suitable method, and can be affixed permanently, in a tearable manner, or in a refastenable manner. The illustrated pants 20 includes the fastening system 80 for refastenably securing the pants about the waist of the wearer. The illustrated fastening system 80 includes first fastening components 82 adapted for refastenable engagement to corresponding second fastening components 84. In one aspect, one surface of each of the first fastening components 82, 84 includes a plurality of engaging elements which project from that surface. The engaging elements of the first fastening components 82 are adapted to repeatedly engage and disengage engaging elements of the second fastening components 84.

The fastening components 82, 84 can include separate elements bonded to the side panels 134, 34, or they can be integrally formed with the side panels. Thus, unless otherwise specified, the term "fastening component" includes separate components which function as fasteners, and regions of materials such as the side panels 34, 134 which function as fasteners. Moreover, a single material can define multiple fastening components to the extent that different regions of the material function as separate fasteners. The fastening components 82, 84 can be located on the side panels 34, 134, between the side panels such as on the absorbent chassis 32, or a combination of the two.

Components, alignment, and articles can be inspected using an infrared inspection system such as that described in U.S. Pat. No. 6,885,451 to Vogt, et al., and in co-pending U.S. patent application Ser. No. 12/580,765, entitled "Disposable Absorbent Articles Incorporating Black-Free Colorant" each of which is incorporated herein by reference to the extent it does not conflict herewith.

Examples of suitable materials from and processes by which components can be constructed and printed can be found in co-pending U.S. patent application Ser. No. 12/023,447, entitled "Printable Elastic Composite," which is incorporated herein by reference to the extent it does not conflict herewith.

Absorbent products are often created from multiple materials and components that typically differ in look and feel. Real cloth underwear, however, is generally created from a single chassis material and waist and leg bands. As a result, the real cloth underwear has a consistent look and feel. With respect to disposable absorbent products made from multiple nonwoven components, consumers generally prefer products that more closely emulate the appearance of real cloth underwear. This desire leads to a need to reduce the actual differences in the appearance of a disposable absorbent across its different materials and components and to create perceptions of a similar look and feel across different materials.

Attempts to produce disposable absorbent products with the look and feel of a real garment have fallen short of delivering on the desired integrated look. To manage costs, elastic panels with one set of material properties are often combined with a central chassis having different material properties. For example, in a closed pant, the elastic panels have a gathered texture, whereas the chassis, because it does not need to stretch, conventionally has a smoother texture. Printing these two different materials with the same desired design results in a significant difference in how the appearance of the printed graphic due to differences in how the ink interacts with the different materials and with the stretch of an elastic panel.

One solution to this problem is to print one or more components to match other components in the disposable absorbent article.

Any printing technique can be employed to apply an ink to the surface of the meltblown facing, such as gravure printing, flexographic printing, screen printing, ink-jet printing, laser printing, thermal ribbon printing, piston printing, etc. In one particular aspect, ink-jet printing techniques are employed to apply an ink to the meltblown facing. Ink-jet printing is a non-contact printing technique that involves forcing an ink through a tiny nozzle (or a series of nozzles) to form droplets that are directed toward the support. Two techniques are generally utilized, i.e., "DOD" (Drop-On-Demand) or "continuous" ink-jet printing. In continuous systems, ink is emitted in a continuous stream under pressure through at least one orifice or nozzle. The stream is perturbed by a pressurization actuator to break the stream into droplets at a fixed distance from the orifice. DOD systems, on the other hand, use a pressurization actuator at each orifice to break the ink into droplets. The pressurization actuator in each system can be a piezoelectric crystal, an acoustic device, a thermal device, etc. The selection of the type of ink jet system varies on the type of material to be printed from the print head. For example, conductive materials are sometimes required for continuous systems because the droplets are deflected electrostatically.

The particular type or style of ink pattern is not a limiting factor of the disclosure, and can include, for example, any arrangement of stripes, bands, dots, or other geometric shape. The pattern can include indicia (e.g., trademarks, text, and logos), floral designs, abstract designs, any configuration of artwork, etc. The pattern can be targeted for a specific class of consumers. For example, in the case of diapers or training pants, the pattern can be in the form of cartoon characters, and so forth. It should be appreciated that the "pattern" can take on virtually any desired appearance. The printing scheme can leave little or no white space, or the printing scheme can leave some or much white space.

The ink generally includes one or more colorants (e.g., pigments, dyes, etc.) that impart a certain color to the facing, such as black, white, yellow, cyan, magenta, red, green, blue, etc. For example, the colorant can be an inorganic and/or organic pigment. Some examples of commercially-available organic pigments that can be used in the present disclosure include those that are available from Clariant Corp. of Charlotte, N.C., under the trade designations GRAPHTOL® or CARTAREN®. Other pigments, such as lake compounds (blue lake, red lake, yellow lake, etc.), can also be employed. Inorganic and/or organic dyes can also be utilized as a colorant. Exemplary organic dye classes include triarylmethyl dyes, monoazo dyes, thiazine dyes, oxazine dyes, naphthalimide dyes, azine dyes, cyanine dyes, indigo dyes, coumarin dyes, benzimidazole dyes, paraquinoidal dyes, fluorescein dyes, diazonium salt dyes, azoic diazo dyes, phenylenediamine dyes, diazo dyes, anthraquinone dyes, trisazo dyes, xanthene dyes, proflavine dyes, sulfonaphthalein dyes, phthalocyanine dyes, carotenoid dyes, carminic acid dyes, azure dyes, acridine dyes, and so forth. One particularly suitable class of dyes includes anthraquinone compounds, which can be classified for identification by their Color Index (CI) number. For instance, some suitable anthraquinones that can be used in the present disclosure, as classified by their "CI" number, include Acid Black 48, Acid Blue 25 (D&C Green No. 5), Acid Blue 40, Acid Blue 41, Acid Blue 45, Acid Blue 129, Acid Green 25, Acid Green 27, Acid Green 41, Mordant Red 11(Alizarin), Mordant Black 13 (Alizarin Blue Black B), Mordant Red 3 (Alizarin Red S), Mordant Violet 5 (Alizarin Violet 3R), Natural Red 4 (Carminic Acid), Disperse Blue 1, Disperse Blue 3, Disperse Blue 14, Natural Red 16 (Purpurin), Natural Red 8, Reactive Blue 2, and so forth.

Prior to application, the colorant is typically dissolved or dispersed in a solvent to form the ink. Any solvent capable of dispersing or dissolving the components is suitable. The concentration of solvent in the ink formulation is generally high enough to allow easy application, handling, etc.

The ink can also include various other components as is well known in the art, such as colorant stabilizers, photoinitiators, binders, solvents, surfactants, humectants, biocides or biostats, electrolytic salts, pH adjusters, etc. Other additives can also be included to improve ink performance, such as a chelating agent to sequester metal ions that could become involved in chemical reactions over time, a corrosion inhibitor to help protect metal components of the printer or ink delivery system, a biocide or biostat to control unwanted bacterial, fungal, or yeast growth in the ink, and a surfactant to adjust the ink surface tension.

In one aspect of the present disclosure, two or more components are printed with a single graphic or pattern to mask the inherent appearance of the materials from which those components are constructed, and/or to mask the physical structure of those components or of the article itself.

The resulting appearance can be created by printing an object graphic, a random graphic, a background pattern, a simulated texture, or some combination of these. The printing spans multiple components and can minimize the area of white and/or unprinted space on the outer surface of the article. The printing can be used to break up areas of white space or to otherwise optimize the use of white space on the article.

Numerous aspects of the present disclosure can be used to accomplish a uniform look. For example, the masking pattern can serve as a primary or background graphic and the overall graphics can include such elements as a waistband, leg bands, object graphics, and random graphics. Although nonwoven materials and components made therefrom typically have a white background, the printing described herein can be done on pigmented substrates such as a pink outer cover and pink elastic panels, or on a combination of pigmented and unpigmented substrates such as a white outer cover with pink elastic panels. The key is that printing is done on at least one material to accomplish a uniform look across multiple materials.

In another aspect of the present disclosure, when printing on material components that do not stretch, that differ in stretch, or that might or might not be fully stretched in use, it is desirable to print a graphic that is not greatly distorted during use as the different materials stretch to differing extents. In addition, materials with variable or non-uniform stretch characteristics in different regions can be printed such that the different regions have a similar appearance. More practically, the materials should provide a similar look when pulled from the package and when worn by a user. One way to accomplish this is to optimize the printed graphic to include identical or substantially similar elements in various sizes. For example, the printed graphic can include stars of at least two sizes such that the smaller stars when stretched resemble the larger stars. This ensures that some of the elements look the same between the outer cover and the elastic panel both when pulled from the package and when worn by the user. In another example, a non-uniform sinusoidal wave, such as one with tall and short heights, and/or with wide and narrow widths, can be used to better mimic the look of both the stretch material in different states and the non-stretch material.

In another aspect of the present disclosure, and as apparent to those skilled in the art, material characteristics of a substrate to be printed should be considered when selecting a substrate, a printing method, an ink, and an intended result.

In typical disposable absorbent article, areas of white or unprinted space on the chassis and the elastic panels tend to emphasize the physical structure of the article by, for example, highlighting seams, inherent textures, and other material features. With the use of printing to mask such texture and physical structures, the areas of white or unprinted space on the chassis and the elastic panels can be used to indicate a uniform look across the article.

In one example of this aspect, both the outer cover and elastic panels of a pant be printed with the same graphic such that the materials from which those components are constructed look different from their original states but now match each other. Once these components are assembled into a pant, the pant takes on a one-piece garment look because the stretch and non-stretch materials look substantially the same. In one example, the components can be printed with thermal knit or ribbed knit pattern.

In another aspect of the present disclosure, one component can be printed to match the inherent appearance of the material from which another component is constructed.

Although the descriptions herein are largely directed toward printing an elastic panel to mask or mimic the appearance of an outer cover, the same disclosure can be applied to printing an outer cover to mask or mimic the appearance of an elastic panel, or to print any component of the article to mask or mimic the appearance of another component in the article.

A uniform look across multiple components can be achieved by mimicking the inherent appearance of one component's non-printed material via printing a replicated inherent appearance on another component. It is not simply replicating a color between different nonwoven materials. The printed component is printed in such a way as to appear to exhibit the inherent appearance of the non-printed component.

When printing on material components that do not stretch, that differ in stretch, or that might or might not be fully stretched in use, it is desirable to print a graphic that is not greatly distorted during use as the different materials stretch to differing extents. In various solutions, the printing is done to replicate either the inherent appearance of the article in its unstretched state, such as just out of a package, or the average stretched state of the article as it is worn by a user.

Additionally, the printed texture graphic can serve as a primary or background graphic and the overall graphics can include such elements as a waistband, leg bands, object graphics, and random graphics. The materials being matched can be pigmented or non-pigmented.

In an alternative aspect of the present disclosure, the printed texture graphic can mimic the texture or appearance of one portion of another component, rather than the specific material from which that component is constructed. For example, the printed texture graphic can be printed on an elastic panel to emulate the gathers in the elastic waistband of the chassis 32 such that an appearance of a uniform elastic waistband is presented.

Further detail with respect to methods for measuring visual and tactile properties, and products exhibiting such properties, can be found in U.S. Patent Application Publication Nos. US2006/0161129 and US2006/0161130 and in U.S. Pat. No. 6,174,303, which are incorporated herein by reference to the extent they do not conflict herewith.

It has been shown that surface printing of differing materials such as a stretch elastic panel and a non-stretch outer cover can successfully look the same if care is taken to create a surface texture on the non-stretch material that looks similar to that of the stretch material when in a relaxed state. The desired texture is arrived at through experimentation with facing basis weight and bond pattern as described in more detail below.

Alternatively, the printed texture graphic on stretch material can be designed such that the stretch material has the appearance of being smoother than it is in a perception of smoothness versus actual smoothness. In one example, a grey heather pattern is printed onto the stretch material of the elastic panel to allow the elastic panel to appear smoother in texture.

In another aspect of the present disclosure, it is undesirable to have the printed texture pattern emulate the inherent appearance of another component if such inherent appearance has an aesthetic cue (e.g., unattractive or rough) that would undermine the desired uniform look of the article. In this aspect, it is often better to use printing to mask the inherent appearances of the various components. In one example, a grey heather pattern is printed onto the stretch material of the elastic panel and an open grey heather pattern is printed onto the non-stretch material of the outer cover to mask the appearance of each component.

It should be noted that the present disclosure encompasses a combination of different printing types as well as a combination of internal and external printing. One or more printing types can be used in a single article, where the printing types include, but are not limited to, digital, flexographic, gravure, contact, non-contact, online, and offline printing. In addition, printing can be surface printing on the outermost layer of a given component, or printing can be on an internal surface or on an internal layer of a given component such that the printing is visible at the surface of that component. For example, an article can be manufactured with external printing on one component and printing sandwiched between materials such as a film and a surface facing on a different component.

In further examples, stretch material such as that which might be employed in an elastic panel can be externally printed, while a non-stretch portion of an outer cover can be internally printed, or vice versa. An article can have both external and internal printing on the garment-facing surface of the article, or alternatively or additionally on the body-facing surface of the article. Barrier material and/or non-barrier material can be printed. Breathable and/or non-breathable material can be printed. Materials with different printing types can be attached directly to each other and can be either the same material (e.g., elastic panel to elastic panel junction) or different materials (e.g., body panels to insert). The materials can vary by thickness, texture, topography, and any other suitable characteristic.

In still further examples, printed random graphics can be combined with registered graphics. Graphics can be integrated on the externally- and internally-printed materials. Printing can be done on pigmented or otherwise-colored material and/or on unpigmented or "white" material.

In one particular aspect of the present disclosure, the elastic panels of a disposable absorbent article are printed on the exterior facing surface of their elastic panel material, while the outer cover of the disposable absorbent article is printed on the film of the outer cover and covered with a nonwoven facing layer. In effect, the article of this aspect is both externally (elastic panels) and internally (outer cover) printed. More specifically, in this aspect the elastic panels are flexographically printed offline. The film of the outer cover is also flexographically printed offline and covered with a nonwoven facing. Both materials are then introduced into the article manufacturing process such that the printing on the elastic panels is aligned with the printing on the outer cover.

In a different particular aspect of the present disclosure, a disposable absorbent article has a flexographically-printed outer cover (internal printing) and a digitally-printed waistband (external printing) on the elastic panels.

The various aspects of the present disclosure can be applied in either machine-direction or cross-direction processes. In one example, an article with a three-piece chassis can include printing on the body panels and the insert. Such an article can be printed digitally on the outer surface of the body panel, such as a back label indicator, and printed internally on the insert. Variations of this example can include any combination of internal, external, digital, flexographic, or any other suitable printing method.

While this disclosure generally describes printing stretch materials with external printing and non-stretch materials with internal printing, the opposite can also be used with stretch materials having internal printing and non-stretch materials having external printing. In addition, both materials can be stretch, both can be non-stretch, both can be internally printed, or both can be externally printed. Additional detail related to printing on various materials and components can be found in U.S. Patent Application Publication No. US 2005/0217791, and in U.S. Pat. Nos. 5,562,037; 5,566,616; 5,501,149; 5,597,642; 5,612,118; and 6,231,715, each of which is incorporated herein by reference to the extent it does not conflict herewith.

In practice, a disposable absorbent article of the present disclosure can have multiple printed components. Materials appropriate for use in manufacturing the outer cover and the elastic panels can be selected as described above. The material used in the manufacture of the outer cover is typically different from the material used in the manufacture of the elastic panels, although this is not a requirement in manufacturing the article. The outer cover in the manufactured article has an outer cover central region positioned generally in the front and/or back waist regions. The outer cover central region does not include a waistband or leg bands. The outer cover central region has an outer cover central region appearance, which is the physical appearance of the outer cover central region. It should be noted that the central regions described herein are arbitrary areas taken to include a swatch or a sample of the printing, texture, or general appearance of an area. Such regions are generally located centrally in the longitudinal direction between the leg openings and the waist opening, and do not include printed waistbands or printed leg bands. Central regions are intended to allow one to compare the appearance of areas of an article. Although illustrated in FIGS. 2, 4, and 5 as being generally ovoid, the central regions can be of any suitable shape.

The elastic panel is printed either before or after attachment to the chassis as described above. The elastic panel can be printed to match the outer cover central region appearance whether or not the outer cover central region is printed. The elastic panel can be printed to match the printing in the outer cover central region, or the elastic panel can be printed to match the outer cover texture of the material from which the outer cover is constructed. In either case, the elastic panel central region is printed to appear identical or substantially similar to the outer cover central region appearance. Second, third, and fourth elastic panels can be manufactured in much the same manner.

Further, the article can be manufactured such that the outer cover central region and the first elastic panel central region have no lateral gap therebetween, or can be disposed such that a lateral gap in printing is present between the regions. In other words, the outer cover central region and the elastic panel central region can be a continuous region of printing or other appearance, or there can be a lateral gap between the outer cover central region and the elastic panel central region. In a specific example, the lateral gap between the outer cover central region and the first elastic panel central region should be less than 15 mm, preferably less than 10 mm, more preferably less than 5 mm, and most preferably 0 mm. It should be noted that some printed graphics, such as those with vertical stripes, can include an inherent lateral gap as part of their patterns. Such inherent lateral gaps are not included herein in the definition of a lateral gap.

In another aspect of the present disclosure, a lateral circumference taken between the waist opening and the top of the leg openings can be seen to cross at least two elastic panels. Each component along the circumference can be printed such that at least a portion of each component is identical or substantially similar in appearance to the other components. In addition, the outer cover, if not on the circumference, can also be printed to be identical or substantially similar in appearance to the other components.

In still another aspect of the present disclosure, the pants 20 can also include a printed waistband and/or printed leg bands as described in co-pending U.S. patent application Ser. No. 12/580,529, entitled "Alignment Of Leg And Waistbands On Disposable Absorbent Article," which is incorporated herein by reference to the extent that it does not conflict herewith.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed is:

1. A method for manufacturing a disposable absorbent article having multiple components, the method comprising:
    providing a first material for use as an outer cover;
    producing a chassis including the outer cover, the outer cover including an outer cover central region having an outer cover central region appearance;
    providing a second material for use as an elastic panel, wherein the second material is different from the first material;
    producing a first elastic panel having a first elastic panel central region;
    printing the first elastic panel central region with a first elastic panel printed graphic; and
    attaching the first elastic panel to the chassis,
        wherein the providing and printing are performed such that the first elastic panel central region gives the appearance of being substantially similar to the outer cover central region appearance;
    wherein the outer cover central region appearance includes an outer cover printed graphic, wherein the outer cover printed graphic is substantially similar to the first elastic panel printed graphic;
    wherein the outer cover printed graphic and the elastic panel graphic each include graphical elements that are substantially similar except for being of at least two sizes when the article is not stretched, and that are substantially similar in size when the article is stretched.

2. The method of claim 1, wherein the outer cover central region appearance includes an outer cover texture appearance, and wherein the first elastic panel printed graphic is printed to appear substantially similar to the outer cover texture appearance.

3. The method of claim 1, wherein the outer cover printed graphic and the first elastic panel printed graphic share a color palette.

4. The method of claim 1, wherein the outer cover printed graphic and the first elastic panel printed graphic share graphical elements.

5. The method of claim 1, wherein the outer cover printed graphic and the first elastic panel printed graphic share a graphic theme.

6. The method of claim 1, wherein the elastic panel printed graphic includes a repetitive pattern.

7. The method of claim 1, wherein the elastic panel printed graphic includes an object graphic.

8. The method of claim 1, wherein the outer cover central region and the elastic panel central region do not include a waistband or a leg band.

9. The method of claim 1, wherein the elastic panel is a side panel.

10. The method of claim 1, wherein the elastic panel is a body panel.

11. The method of claim 1, wherein the outer cover is stretchable.

12. The method of claim 1, wherein the outer cover or the elastic panel is pigmented.

13. The method of claim 1, further comprising:
    producing a second elastic panel having a second elastic panel central region;
    printing the second elastic panel central region with a second elastic panel printed graphic, wherein the second elastic panel printed graphic is substantially similar to the first elastic panel printed graphic; and
    attaching the second elastic panel to the chassis,
        wherein the printing are performed such that the second elastic panel central region appears to be substantially similar to the outer cover central region appearance.

14. The method of claim 1, wherein the outer cover central region and the first elastic panel central region have no lateral gap in printing therebetween.

* * * * *